United States Patent
Kwon (10) Patent No.: US 6,522,916 B1
(45) Date of Patent: Feb. 18, 2003

(54) TELEMETRIC SYSTEM FOR FETAL CARE

(75) Inventor: Ki Chul Kwon, 349-61, Rimun-Dong, Dongdaemun-Ku, Seoul (KR)

(73) Assignees: Ki Chul Kwon, Seoul (KR); Neode Co., Ltd., Seoul (KR)

( * ) Notice: Subject to any disclaimer, the term of this patent is extended or adjusted under 35 U.S.C. 154(b) by 123 days.

(21) Appl. No.: 09/689,942

(22) Filed: Oct. 12, 2000

(30) Foreign Application Priority Data

May 9, 2000 (KR) .......................................... 2000-24520

(51) Int. Cl.[7] .............................................. A61B 5/0444
(52) U.S. Cl. ......................... 600/511; 607/902; 128/920
(58) Field of Search ................................ 600/511, 300, 600/301, 302, 303, 304, 588; 128/920; 607/902

(56) References Cited

U.S. PATENT DOCUMENTS

| | | | |
|---|---|---|---|
| 5,431,171 A | | 7/1995 | Harrison et al. |
| 5,609,156 A | * | 3/1997 | Keith et al. ................. 128/670 |
| 5,715,823 A | * | 2/1998 | Wood et al. ................. 128/904 |
| 5,817,035 A | * | 10/1998 | Sullivan ...................... 600/588 |
| 5,891,035 A | * | 4/1999 | Wood et al. ................. 600/437 |
| 5,935,061 A | * | 8/1999 | Acker et al. ................. 600/304 |
| 5,957,855 A | * | 9/1999 | Oriol et al. .................. 600/511 |
| 5,995,756 A | * | 11/1999 | Herrmann ................... 395/712 |
| 6,254,537 B1 | * | 7/2001 | Nguyen ....................... 600/300 |
| 6,302,844 B1 | * | 10/2001 | Walker et al. ............... 600/300 |

* cited by examiner

*Primary Examiner*—John Rivell
(74) *Attorney, Agent, or Firm*—Akin, Gump, Strauss, Hauer & Feld, L.L.P.

(57) ABSTRACT

A telemetric system for fetal health, which receives data of a pregnant woman or a fetus of the pregnant woman, analyzes the received data and reporting a diagnosis result in order to make a diagnosis of fetal health without the pregnant woman calling on a hospital.

The telemetric system for fetal care including a telemetric server for providing first analysis data by analyzing data a data offering client terminal having a data input unit on a communications network, a data diagnosis client receiving the source data from the telemetric server and generating a second analysis data or a final diagnosis result, the telemetric server receiving the second analysis data or the final diagnosis result form the data diagnosis client and transmitting the second analysis data or the final diagnosis result to a result report unit and a Web server managing unit for informing and displaying the second analysis data or the final diagnosis result.

23 Claims, 5 Drawing Sheets

TELEMETRIC SYSTEM FOR FETAL CARE

BACKGROUND OF THE INVENTION

1. Technical Field

The present invention relates to a system for receiving data of a pregnant woman or a fetus of the pregnant woman, analyzing the received data and reporting a diagnosis result, more particularly to a telemetric system for fetal care which may make a diagnosis of fetal health without the pregnant woman calling on a hospital.

2. Description of the Prior Art

Generally, a pregnant woman visits an obstetrical hospital regularly for examining cardiac sound, fetal heart rate (HR), fetal movement and uterine contraction (UC), needed for fetal health, from 28 weeks after pregnant to parturition. The UC and the fetal movement are referenced right before parturition or in terminal of pregnancy.

However, it is common that the fetal HR data is used for fatal care during a period not corresponding to the right-before parturition or terminal of pregnancy. At this time, the pregnant woman should spend much time to call on the obstetrical hospital personally.

SUMMARY OF THE INVENTION

Therefore, the present invention is designed to overcome such problems of the prior art. An object of the present invention is to provide a telemetric system for fetal care including a telemetric server for providing first analysis data by analyzing source data from a data offering client terminal having a data input unit on a communications network, a data diagnosis client for receiving the source data from the telemetric server and generating a second analysis data or a final diagnosis result, the telemetric server receiving the second analysis data or the final diagnosis result form the data diagnosis client and transmitting the second analysis data or the final diagnosis result to a result report unit and a Web server managing unit for informing and displaying the second analysis data or the final diagnosis result.

Another object of the present invention is to provide a method of implementing the above telemetric system.

Still another object of the present invention is to provide a programmed computer system and a computer program product for executing the above method of the present invention.

In order to accomplish the above object, the present invention provides a telemetric system for fetal care comprising a data offering client terminal including a communications interface unit which is accessible to communications network and a data input unit for converting source data generated by examining health of a pregnant woman and a fetal health of the pregnant woman to digital data which is transmittable through the communications network; and a telemetric server for receiving the source data from the data offering client terminal connected to the communications network, generating first analysis data by provisional diagnosis of the source data, displaying the generated first analysis data on a homepage, transmitting the first analysis data to a data diagnosis client according to a request of the data diagnosis client, receiving a final diagnosis result related to the first analysis data from the data diagnosis client, displaying the final diagnosis result on the homepage again, reporting the final diagnosis result to the data offering client terminal, and constructing a database with the final diagnosis result.

In this embodiment, the source data may include fetal movement data, fetal heart rate (HR) data and uterine contraction (UC) data of the pregnant woman, generated by examining the pregnant woman and the fetal health of the pregnant woman.

The telemetric server may include a database means for storing the inputted source data, the first analysis data generated after analyzing the source data, and the final diagnosis result; a main processor for receiving the source data stored in the database means, generating the first analysis data with a pre-inputted diagnosis module in a data analysis program, storing the generated first analysis data into the database means, determining whether a fetus is normal or not with the first analysis data, and requesting result report means to give a final report when the fetus is abnormal; result report means for receiving a request to report the final report about the abnormal fetus from the main processor and providing data of informing that the fetus is abnormal to the data offering client through the communications network; and Web server managing means for transmitting the first analysis data to the data diagnosis clients through the communications network, receiving the final diagnosis result from the data diagnosis clients, stores the final diagnosis result in the database means and displaying the data stored in the database means on the homepage in order to provide all diagnosis processes from the source data to the final diagnosis result.

The data analysis program in the main processor may include a fetal HR analysis module for evaluating Long-term/Short-term MMR (Mean Minute Range) with use of the fetal HR data extracted from the source data; a variability analysis module for analyzing a period of the UC data in order to set a time basis, calculating a fetal HR baseline with accumulating the fetal HR data extracted from the source data according to the time basis, and determining a pulse situation from the fetal HR baseline; and a fetal HR acceleration/deceleration analysis module for determining whether a fetal HR accelerates or decelerates with the fetal HR data.

The fetal HR acceleration/deceleration analysis module may include a module for detecting acceleration of the fetal HR and a module for detecting deceleration of the fetal HR.

The result report means may display the final diagnosis result on the homepage through the Web server managing means for providing the final diagnosis result to a plurality of clients, and reports the final diagnosis result to the data offering client by any or all of e-mail, phone and ARS (Auto Response Service).

In order to obtain the above object, the present invention provides a telemetric method for fetal care including the steps of: receiving a source data from pregnant woman and a fetal of the pregnant woman through a data offering client terminal which includes an data input unit and dividing the received source data into fetal heart rate (HR) data and uterine contraction (UC) data of the pregnant woman; b) making a provisional diagnosis for producing a first analysis data by analyzing the fetal HR data and the UC data; c) transmitting the first analysis data to Web server managing means to be displayed on a homepage and transmitting the first analysis data to result report means in case that the provisional diagnosis finds an abnormal result in order to report the abnormal result to the data offering client; and d) providing the first analysis data to a data diagnosis client according to a request of the data diagnosis client, receiving and storing a final diagnosis result from the data diagnosis client, transmitting the final diagnosis result to the Web server managing means, and reporting the final diagnosis result including normal/abnormal situation information to the data offering client.

In order to achieve the above object, the present invention provides a record medium including a telemetric diagnosis program for fetal care which transmits data from/to a client terminal and a Web server through a communications network, processing and analyzing the data and informing analyzed results, the record medium comprising a source data dividing process for receiving source data from a pregnant woman and a fetal of the pregnant woman through a data offering client terminal which includes an data input unit and dividing the received source data into fetal heart rate (HR) data and uterine contraction (UC) data of the pregnant woman; a provisional diagnosis process for producing a first analysis data by analyzing the fetal HR data and the UC data; a provisional diagnosis reporting process for transmitting the first analysis data to Web server managing means to be displayed on a homepage and transmitting the first analysis data to result report means in case that the provisional diagnosis finds an abnormal result in order to report the abnormal result to the data offering client; and a final diagnosis result process for providing the first analysis data to a data diagnosis client according to a request of the data diagnosis client, receiving a final diagnosis result from the data diagnosis client, storing the final diagnosis result in a database, transmitting the final diagnosis result to the Web server managing means, and reporting the final diagnosis result including normal/abnormal situation information to the data offering client.

In the above two embodiments, the first analysis data may include variability data for determining fetal hypoxia and the first analysis data may further include data about fetal HR acceleration, prolonged fetal HR acceleration, variable fetal HR deceleration, prolonged fetal HR deceleration, early fetal HR deceleration and late fetal HR deceleration for diagnosis of a fetal HR acceleration/deceleration by using the fetal HR data extracted from the source data.

The step b) and the provisional diagnosis process may further includes the steps of 1) calculating a Long-term MMR (Mean Minute Range) and a Short-term MMR from the fetal HR data; 2) removing noise from the fetal HR data; and 3) finding a stand deviation of the fetal HR data without noise.

The Long-term MMR is preferably a value calculated by generating a first Long-term maximum variation value by converting a peak of the fetal HR data for a predetermined time into a msec unit, generating a second Long-term maximum variation value by converting a nadir of the fetal HR data for a predetermined time into a msec unit, accumulating and averaging differences between the first Long-term maximum variation value and the second Long-term maximum variation value.

The Short-term MMR is preferably a value calculated by generating a first Short-term maximum variation value by converting a peak of the fetal HR data for a pre determined time into a msec unit, generating a second Short-term maximum variation value by converting a nadir of the fetal HR data for a predetermined time into a msec unit, accumulating and averaging differences between the first Short-term maximum variation value and the second Short-term maximum variation value.

The step b) and the provisional diagnosis process may further include the steps of determining that the fetal HR data is normal when being centered on a baseline of the fetal HR data, tachycardia when being faster than the normal HR data, and bradycardia when being slower than the normal HR data according to the predetermined baseline and determining variability data with the standard deviation of the baseline according to predetermined criteria.

The step b) and the provisional diagnosis process may further include the step of determining whether the fetal HR data is normal or not, there is the fetal HR acceleration or not, and there is the prolonged fetal HR acceleration or not by detecting a wave of the fetal HR data, determining where the wave terminates and probing a peak in the nadir area of the wave.

The step b) and the provisional diagnosis process may further include the steps of detecting a fetal HR deceleration wave by comparing the baseline of the fetal HR data with a basic fetal HR; and detecting the variable fetal HR deceleration, the prolonged fetal HR deceleration, the early fetal HR deceleration and the late fetal HR deceleration in the fetal HR data with use of the fetal HR deceleration wave.

The step d) and the final diagnosis result process may further include the steps of storing the final diagnosis result transmitted from the data diagnosis client into database means; and sending the final diagnosis result to the result report means and the Web server managing means in order to report the final diagnosis result to the data offering client with use of the result report means and display the final diagnosis result on the homepage through the Web server managing means.

The data diagnosis clients may include a first data diagnosis client for receiving and analyzing the first analysis data made in the step b) and generating second analysis data and a second data diagnosis client for collectively analyzing the source data and the second analysis data and producing the final diagnosis result.

In order to achieve the above object, the present invention provides a record medium including a telemetric diagnosis program for fetal care which transmits data from/to a client terminal and a Web server through a communications network, processing and analyzing the data and informing analyzed results, the record medium comprising a source data dividing process for receiving source data from a pregnant woman and a fetal of the pregnant woman through a data offering client terminal which includes an data input unit and dividing the received source data into fetal heart rate (HR) data and uterine contraction (UC) data of the pregnant woman; a provisional diagnosis process for producing a first analysis data by analyzing the fetal HR data and the UC data; a provisional diagnosis reporting process for transmitting the first analysis data to Web server managing means to be displayed on a homepage and transmitting the first analysis data to result report means in case that the provisional diagnosis finds an abnormal result in order to report the abnormal result to the data offering client; and a final diagnosis result process for providing the first analysis data to a data diagnosis client according to a request of the data diagnosis client, receiving a final diagnosis result from the data diagnosis client, storing the final diagnosis result in a database, transmitting the final diagnosis result to the Web server managing means, and reporting the final diagnosis result including normal/abnormal situation information to the data offering client.

BRIEF DESCRIPTION OF THE DRAWINGS

These and other features, aspects, and advantages of the present invention will become better understood with regard to the following description, appended claims, and accompanying drawings, in which like components are referred to by like reference numerals. In the drawings:

DETAILED DESCRIPTION OF THE PREFERRED EMBODIMENT

Hereinafter, preferred embodiments of the present invention will be described in detail with reference to the accompanying drawings.

The present invention employs a configuration of a telemetric system for fetal care in which a data offering client terminal having a data input unit is connected to a wire/wireless communications network, to which a telemetric server for analyzing source data is also connected.

The present invention suggests, as a preferred embodiment, a method of receiving source data from the data input unit of the data offering client terminal, generating first analysis data by a provisional diagnosis of the source data, providing the first analysis data to a data diagnosis client according to a request of the data diagnosis client and displaying a final diagnosis result generated by the data diagnosis client on a homepage such that result report means transmits the final diagnosis result together with normal/abnormal information through the communications network in order to provide a telemetric diagnosis service to a user who may access to the telemetric server through the communications network, and a system implementing the method as another preferred embodiment.

The present invention also suggests still another embodiment of the system, in which the data diagnosis client is provided on the communications network as an independent server or installed in the telemetric server for fetal care as a program.

Also, the desirable embodiments of the present invention include a programmed computer system and a computer program product for executing the method of the present invention. In the computer system embodiment, a command set for executing the method may reside in at least one memory (RAM). Also, the commend set may be stored, for example, in other computer memory such as a disk drive in a form of a computer program product until the computer system needs it.

Figure 1:
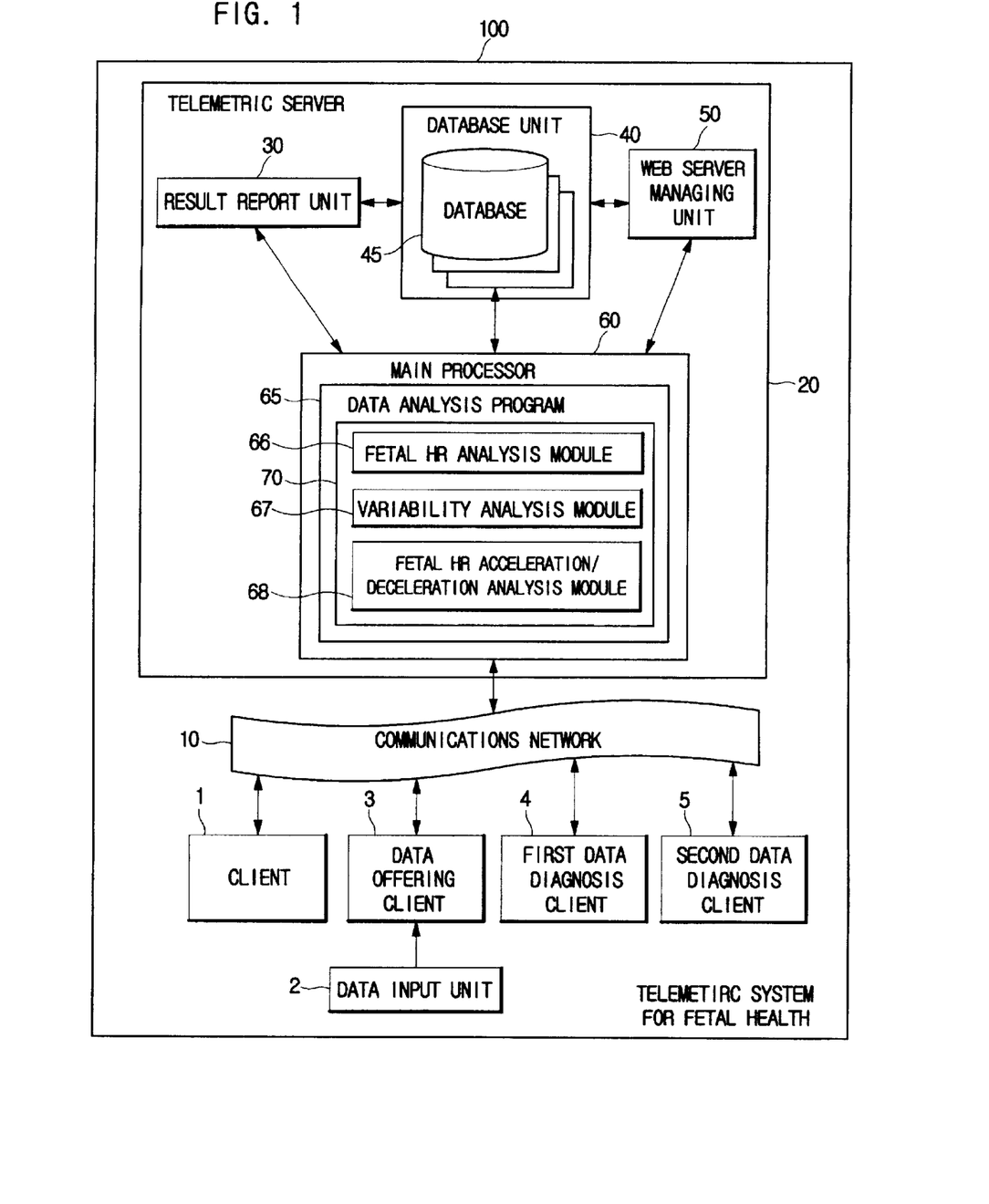
FIG. 1 shows an overall configuration of a telemetric system for fetal care in accordance with the present invention.

FIG. 1 shows an overall configuration of the telemetric system for fetal care in accordance with the present invention.

Referring to the figure, a telemetric server 20 of the present invention is connected to a communications network 10 which connects a plurality of clients 1, a data offering client 3 including a data input unit 2, a first data diagnosis client 4 and a second data diagnosis client 5.

The telemetric server 20 receives source data from the data input unit 2 of the data offering client 3 through the communications network 10, stores the received source data into a database 45 of a database unit 40, processes the stored source data using a diagnosis process module 70 of a data analysis program 65 included in a main processor 60, and generates the first analysis data.

The telemetric server 20 comprises the database unit 40, the main processor 60 and a Web server managing unit 50. The database unit 40 includes the database 45 for storing the source data, which includes fetal movement data, fetal heart rate (HR) data and uterine contraction data, analysis data and a final diagnosis result generated by analysis of the source data. The main processor 60 receives the source data stored in the database 45 and processes the source data with pre-inputted diagnosis process module. The Web server managing unit 50 receives the first analysis data and the final diagnosis result from the main processor 60 and displays the data on a homepage in order to provide the data to a plurality of the clients 1 who access the homepage.

The telemetric server 20 plays a role of a mediation server, which receives the source data from the data offering client 3, generates the first analysis data to be provided to the data diagnosis clients 4, 5, receives the diagnosis result from the data diagnosis clients 4, 5, displays the received diagnosis result on the homepage through the Web server managing unit 50, and reports the diagnosis result to the data offering client 3 through the result report unit 30.

The diagnosis process module 70 includes a fetal HR analysis module 66, a variability analysis module 67 and a fetal HR acceleration/deceleration analysis module 68 and receives the source data and generates the first analysis data.

Besides, the first data diagnosis client 4 and the second data diagnosis client 5 receive the first analysis data through the communications network 10, analyze the received first analysis data and generate the final diagnosis result.

The first data diagnosis client 4 analyzes the first analysis data and then generates second analysis data. The first data diagnosis client 4 then transmits the second analysis data to the telemetric server 20. The telemetric server 20 stores the second analysis data into the database 45 of the database unit 40.

Also, the second data diagnosis client 5 generates the final diagnosis result with reference to the second analysis data generated by the first data diagnosis client 4 together with the first analysis data. The second data diagnosis client 5 then transmits the final diagnosis result to the telemetric server 20, which stores the final diagnosis result into the database 45 of the database unit 40.

Here, the diagnosis process of the first data diagnosis client 4 and the second data diagnosis client 5 may be provided as a programmed product and a kind of server.

In this specification, it is provided that there are two data diagnosis clients in which the first data diagnosis client 4 is a fetal HR specialist and the second data diagnosis client 5 is a doctor in a hospital. However, there can be only one data diagnosis client or a plurality of clients more than two having different diagnosis courses.

In addition, the data diagnosis clients 4, 5 may be a server that generates the final diagnosis result in linkage with the telemetric server 20.

The diagnosis results generated by the first data diagnosis client 4 and the second data diagnosis clients 5 and stored in the database unit 40 are transmitted to the Web server managing unit 50 and displayed on the homepage.

Moreover, if the first data diagnosis client 4 and the second data diagnosis client 5 generate that the second analysis data or the final diagnosis result is abnormal (or, the fetus has an abnormal factor), the second analysis data or the final diagnosis result is transmitted to the result report unit 30. The result report unit 30 then reports the second analysis data or the final diagnosis result to the pregnant woman who has provided the data. The result report unit 30 displays the second analysis data or the final diagnosis result on the homepage through the Web server managing unit 50 and reports it to the pregnant woman by any or all of an e-mail, a telephone or ARS (Auto Response Service).

Figure 2:
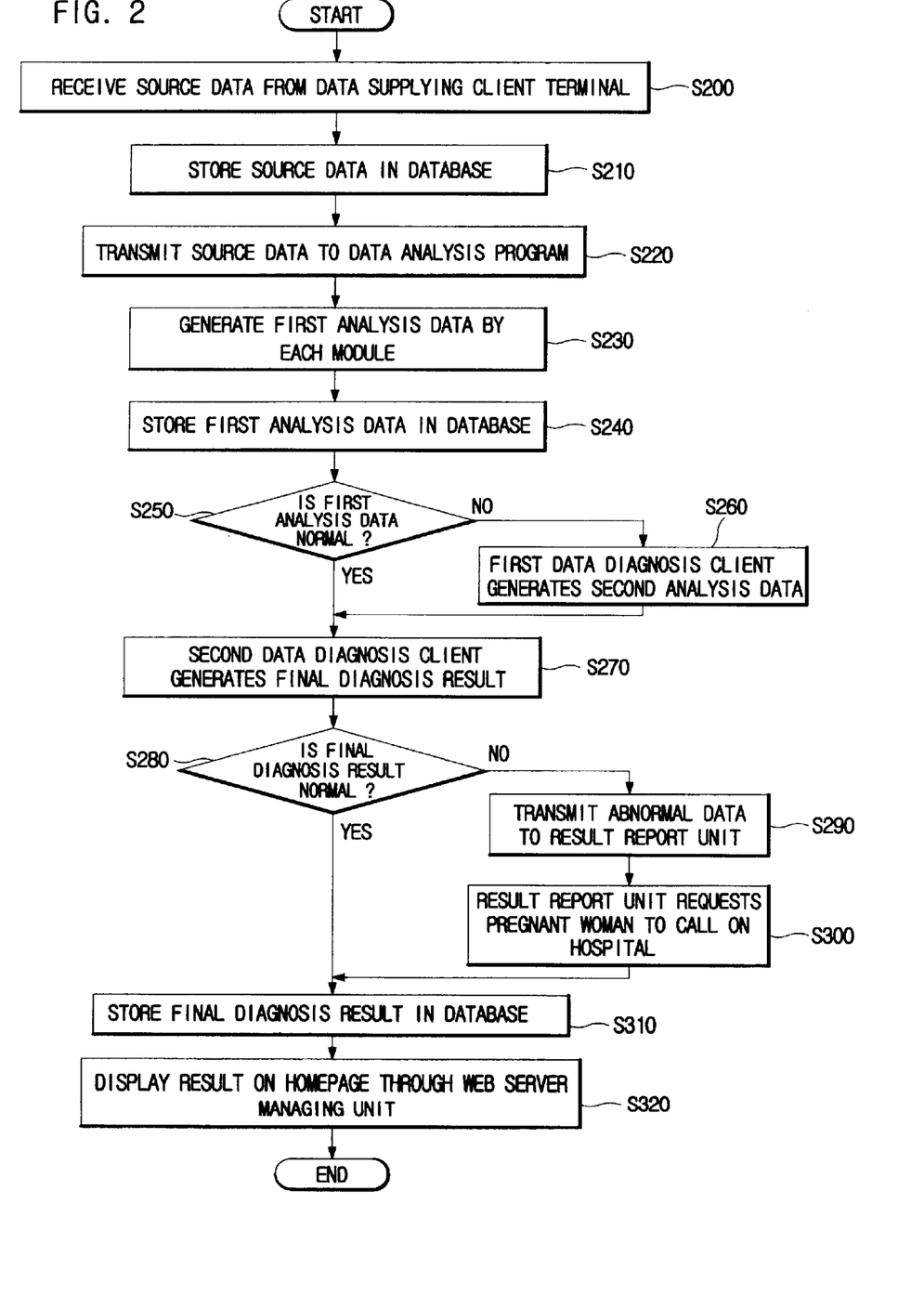
FIG. 2 is a flow chart for illustrating the telemetric system for fetal care in accordance with the present invention.

FIG. 2 is a flow chart for illustrating the telemetric system for fetal care in accordance with the present invention.

Referring to the figure, in brief, the data diagnosis clients are composed of the first data diagnosis client and the second data diagnosis client. The first data diagnosis client receives the first analysis data, which has been analyzed from the source data and generates second analysis data. The second data diagnosis client receives the first analysis data and the second analysis data and generates the final diagnosis result, which may be sent to the pregnant woman.

Hereinafter, the overall operation of the telemetric system for fetal care in accordance with the present invention is explained.

The main processor of the telemetric server receives the source data from the data offering client having the data input unit through the communications network S200 and stores the received source data into the database S210.

The source data stored in the database is transmitted to the data analysis program included in the main processor S220. The data analysis program then processes the source data in each module and generates the first analysis data S230. The first analysis data is stored in the database of the database unit S240. The main processor determines whether the first analysis data is normal or abnormal S250.

Here, the first analysis data, a kind of a provisional diagnosis data, is a basic data for the data diagnosis clients to download and analyze again.

If the main processor determines that the first analysis data is abnormal, the first data diagnosis client generates the second analysis data S260. If the main processor determines that the first analysis data is normal, the second data diagnosis client generates the final diagnosis result by analyzing the first analysis data and, if required, the second analysis data S270.

The main processor determines whether the final diagnosis result is normal or not S280. If the final diagnosis result is abnormal, the main processor transmits the abnormal data to a result report unit S290 and the result report unit requests the pregnant woman to call on the hospital S300.

If the final diagnosis result is normal, the main processor receives the final diagnosis result from the second data diagnosis client and stores the final diagnosis result into the database S310. Then, the main processor displays the final diagnosis result on the homepage with use of the Web server managing unit S320 in order to provide the final diagnosis data to a plurality of clients who access the homepage.

Figure 3:
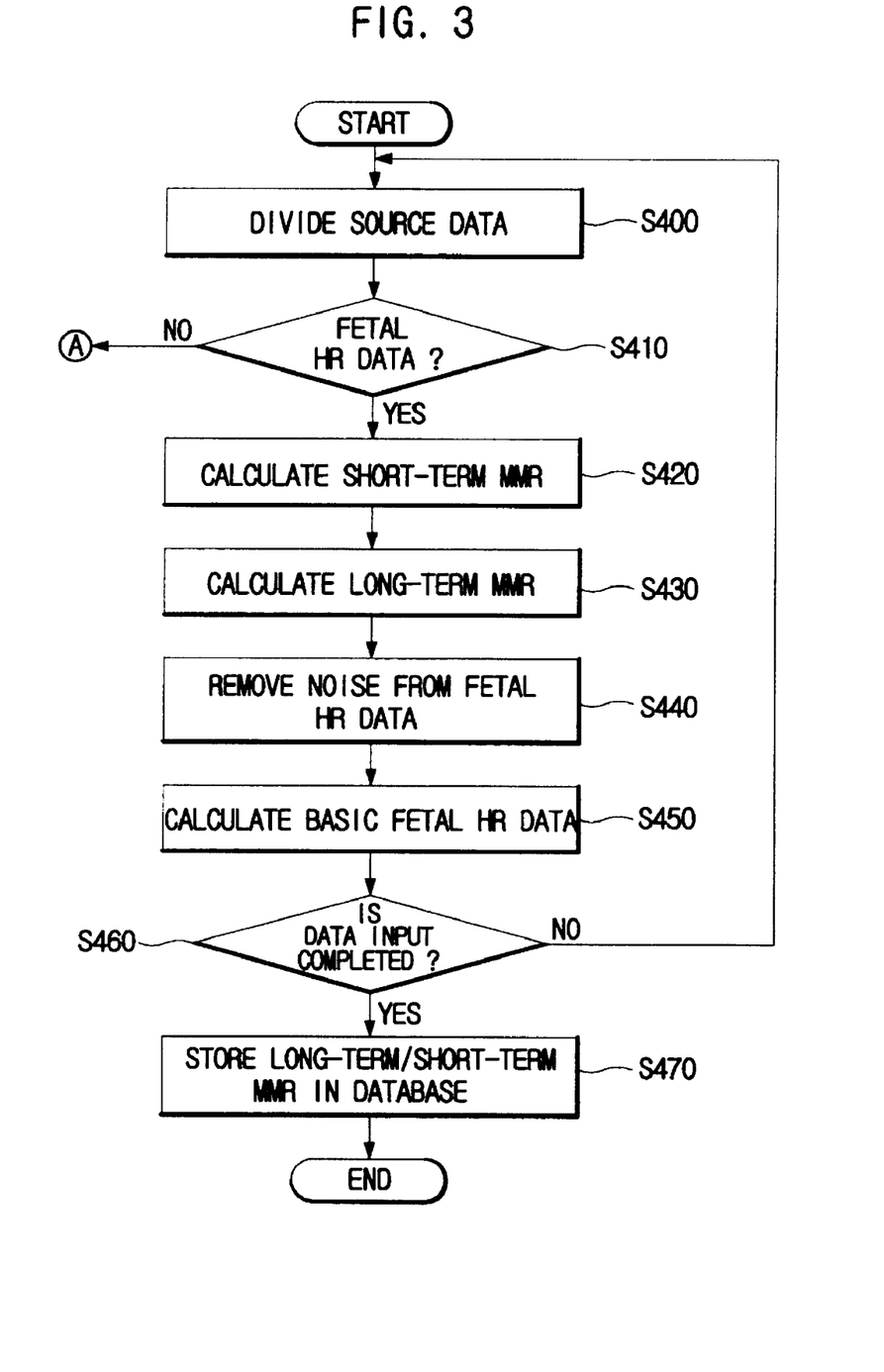
FIG. 3 is a flow chart for illustrating an operation of a fetal HR analysis module in a fetal HR data analysis program in accordance with the present invention.

FIG. 3 is a flow chart for illustrating an operation of the fetal HR analysis module included in the data analysis program in accordance with the present invention.

The fetal HR data analysis program includes the fetal HR analysis module for evaluating Long-term /Short-term MMR (Mean Minute Range) using the fetal HR data extracted from the source data and a module for generating the first analysis data with use of the fetal HR data inputted at every time interval according to a period of the UC data extracted from the source data.

The first analysis data may include variability data for determining fetal hypoxia and may further include data about fetal HR acceleration, prolonged fetal HR acceleration, variable fetal HR deceleration, prolonged fetal HR deceleration, early fetal HR deceleration and late fetal HR deceleration for diagnosis of the fetal HR acceleration/deceleration by using the fetal HR data extracted from the source data.

The main processor divides the source data transmitted from the data input unit of the data offering client terminal into the UC data and the fetal HR data S400. The main processor then determines whether the divided source data is the fetal HR data or not S410.

If the divided source data is not the fetal HR data, the process moves to the step S500 of setting the time basis using the UC data.

If the divided source data is the fetal HR data, the Short-term MMR (Mean Minute Range) and the Long-term MMR are calculated with calculation formulas, which are previously inputted in the fetal HR analysis module of the data analysis program S420, S430.

Here, the Short-term MMR is a value calculated by generating a first Short-term maximum variation value by converting a peak of the fetal HR data for a predetermined time into a msec unit, generating a second Short-term maximum variation value by converting a nadir of the fetal HR data for a predetermined time into a msec unit, accumulating and averaging differences between the first Short-term maximum variation value and the second Short-term maximum variation value.

The Long-term MMR is a value calculated by generating a first Long-term maximum variation value by converting a peak of the fetal HR data for a predetermined time into a msec unit, generating a second Long-term maximum variation value by converting a nadir of the fetal HR data for a predetermined time into a msec unit, accumulating and averaging differences between the first Long-term maximum variation value and the second Long-term maximum variation value.

And then, the data analysis program 65 removes noise from the fetal HR data S440 and calculates basic fetal HR data S450.

At this time, the data analysis program 65 regards the fetal HR data as the noise when the fetal HR data reaches a specific value such as 0 or 255. The data analysis program 65 also regards the fetal HR data as a noise when the current fetal HR data is more than 2 times of the baseline or less than a half of the baseline.

Above numerical values in extracting the noise are just examples in this embodiment and any change will be possible.

On the other hands, the basic fetal HR data is the baseline, from which the noise and the fetal HR acceleration/deceleration data have been removed. The basic fetal HR data is temporarily stored for future use after removing the noise.

The step S450 for calculating the basic fetal HR data may further include the step of finding a standard deviation of the fetal HR data (not show in the figure).

Then, the data analysis program 65 determines whether the input of the source data is completed S460. If the input of the source data is completed, the data analysis program 65 stores the Long-term/Short-term MMR into the database S470. If the source data is not completely inputted, the data analysis program 65 returns to the step of dividing the source data S400.

Figure 4:
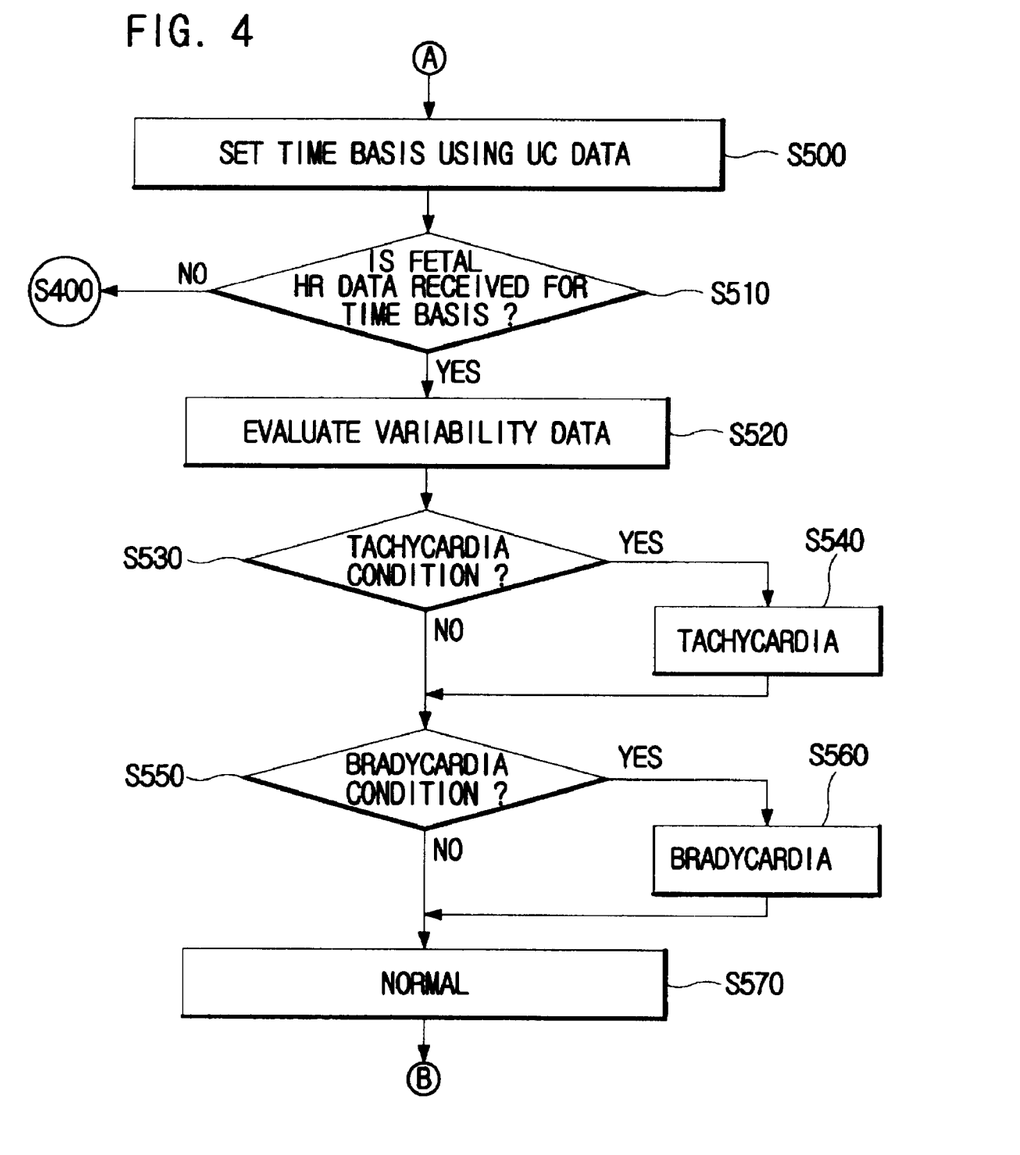
FIG. 4 is a flow chart for illustrating an operation of a variability analysis module in a fetal HR data analysis program in accordance with the present invention.

FIG. 4 is a flow chart for illustrating operation of the variability analysis module in the fetal HR data analysis program in accordance with the present invention.

In FIG. 3, the module of producing the first analysis data includes a first process of setting a time basis in consideration of a period of the UC data extracted from the source data and calculating the baseline with accumulating the fetal HR data extracted from the source data per the time basis, and a second process of generating the first analysis data through the variability analysis module for determining a pulse situation from the baseline and the fetal HR acceleration analysis module for analyzing the fetal HR acceleration/deceleration situation from the fetal HR data. The second process also further includes the step of determining that the fetal HR data is normal when being centered on a baseline of the fetal HR data, tachycardia when being faster than the normal HR data, and bradycardia when being slower than the normal HR data according to the predetermined baseline and the step of determining variability data with the standard deviation of the baseline according to predetermined criteria.

Now, the operation illustrated in the flow chart in FIG. 4 is described.

At first, the variability analysis module goes through the step S400 of dividing the source data in FIG. 3.

The variability analysis module in the fetal HR data analysis program then divides the source data into the fetal HR data and the UC data and extracts the time basis with use of a period of the UC data.

The variability analysis module sets the time basis with use of the UC data S500 and determines whether the fetal HR data is received for the time basis S510.

If the variability analysis module receives the fetal HR data corresponding to the time basis, the variability analysis module evaluates the variability data S520 and determines whether the fetal HR data is in a tachycardia condition S530.

In case that the variability analysis module does not receive the fetal HR data corresponding to the time basis, the variability analysis module determines that the fetal HR data is tachycardia if the fetal HR data is included in the tachycardia condition S540, else, the variability analysis module determines again whether the fetal HR data is included in the bradycardia condition S550.

If the fetal HR data satisfies the bradycardia condition, the variability analysis module determines the fetal HR data is bradycardia S560. While, if the fetal HR data does not satisfies the bradycardia condition, the variability analysis module determines that the fetal HR data is normal S570.

Here, the tachycardia condition means that the inputted baseline is above 160 and at least 10 minutes later from the first examination. The bradycardia condition means that the inputted baseline is below 110 and at least 10 minutes later from the first examination.

The numerical values of the tachycardia and the bradycardia are only examples of this embodiment of the present invention and may be changed.

Figure 5:
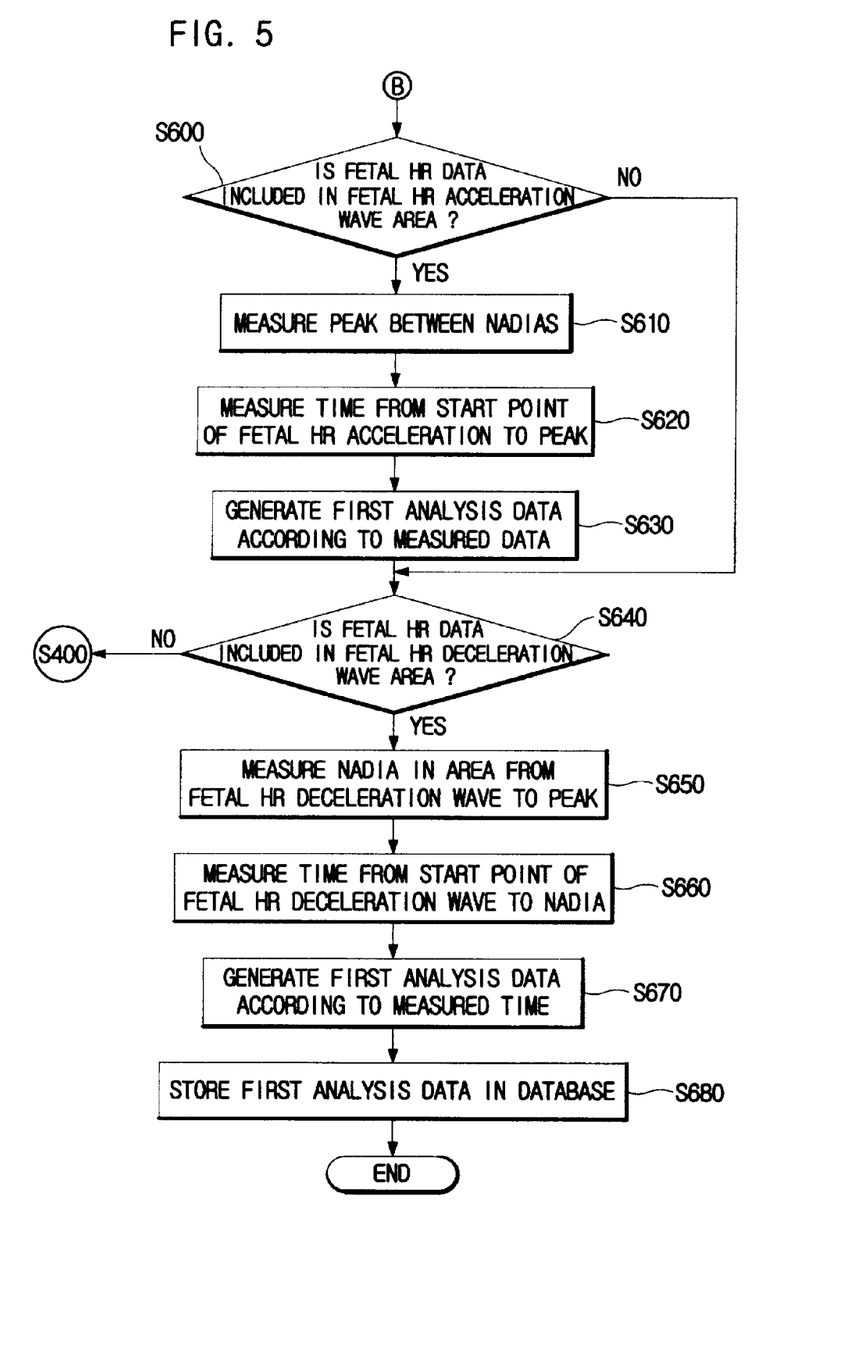
FIG. 5 is a flow chart for illustrating an operation of a fetal HR acceleration/deceleration module in the fetal HR data analysis program in accordance with the present invention.

FIG. 5 is a flow chart for illustrating an operation of the fetal HR acceleration/deceleration module in the fetal HR data analysis program in accordance with the present invention.

FIG. 5 illustrates a process of determining the fetal HR acceleration/deceleration condition through the fetal HR acceleration/deceleration module following the process of FIG. 4.

The fetal HR acceleration/deceleration module includes a fetal HR acceleration detecting module and a fetal HR deceleration detecting module.

The fetal HR acceleration detecting module includes the steps of detecting a wave of the fetal HR data, determining where the wave terminates, probing a peak in the nadir area of the wave, and then determining whether the fetal HR data is normal or not, whether there is the fetal HR acceleration or not and whether there is the prolonged fetal HR acceleration or not.

The fetal HR deceleration detecting module includes the steps of detecting a deceleration wave by comparison of the baseline with the basic fetal HR data and determining the variable fetal HR deceleration, the prolonged fetal HR deceleration, the early fetal HR deceleration and the late fetal HR deceleration with use of the deceleration wave.

The flow chart in FIG. 5 is explained as follows.

The fetal HR acceleration/deceleration module in the fetal HR analysis program determines whether the fetal HR data is included in the fetal HR acceleration wave area S600. If the fetal HR data is included in the fetal HR acceleration wave area, the fetal HR acceleration/deceleration module measures a peak between nadirs and stores the measured peak temporarily S610. The fetal HR acceleration/deceleration module then measures and stores a time taken from a start point of the fetal HR acceleration to the peak S620 and then generates the first analysis data according to the measured time S630.

In case that the fetal HR data is not included in the fetal HR acceleration wave area or after the fetal HR acceleration/deceleration module generates the first analysis data according to the measured time S630, the fetal HR acceleration/deceleration module determines whether the fetal HR data is included in the fetal HR deceleration wave area S640. If the fetal HR data is included in the fetal HR deceleration wave area, the fetal HR acceleration/deceleration module measures a nadir in an area from the fetal HR deceleration wave to the peak and stores the measured nadir S650.

The fetal HR acceleration/deceleration module then measures the time taken from a start point of the fetal HR deceleration wave to the nadir S660, generates the first analysis data according to the measured time S670, and stores the first analysis data into the database S680. If the fetal HR data is not included in the fetal HR deceleration wave area, the process returns to the step S400.

As described above, the present invention gives an advantage that a pregnant woman may consult a doctor for the fetal health through the data offering client terminal including the data input unit at home without seeing the doctor. In fact that the pregnant woman should call on a hospital at early pregnancy and right before the delivery, the present invention may be more useful for the woman in the middle period of the pregnancy.

The present invention provides another advantage that not only the pregnant woman but also a plurality of other clients connected to the communications network may refer to the source data and the diagnosis result by accessing the homepage.

The present invention with above advantages also improves efficiency of the diagnosis by obtaining the first analysis data through the telemetric server with the source data, transmitting the first analysis data to the first and second data diagnosis clients through the communications network, and receiving the final diagnosis result from the first and second data diagnosis clients.

The telemetric system for fetal care according to the present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A telemetric system for fetal care comprising:
   a data offering client terminal including a communications interface unit which is accessible to communications network and a data input unit for converting source data generated by examining health of a pregnant woman and a fetal health of the pregnant woman to digital data which is transmittable through the communications network; and
   a telemetric server for receiving the source data from the data offering client terminal connected to the communications network, generating first analysis data by provisional diagnosis of the source data, displaying the generated first analysis data on a homepage, transmitting the first analysis data to a data diagnosis client according to a request of the data diagnosis client, receiving a final diagnosis result related to the first analysis data from the data diagnosis client, displaying the final diagnosis result on the homepage again, reporting the final diagnosis result to the data offering client terminal, and constructing a database with the final diagnosis result.

2. The telemetric system for fetal care as claimed in claim 1,
   wherein the source data includes fetal movement data, fetal heart rate (HR) data and uterine contraction (UC) data of the pregnant woman, generated by examining health of the pregnant woman and the fetal health of the pregnant woman.

3. The telemetric system for fetal care as claimed in claim 2, wherein the telemetric server comprises:
   database means for storing the inputted source data, the first analysis data generated after analyzing the source data, and the final diagnosis result;
   a main processor for receiving the source data stored in the database means, generating the first analysis data with a pre-inputted diagnosis module in a data analysis program, storing the generated first analysis data into the database means, determining whether a fetus is normal or not with the first analysis data, and requesting result report means to give a final report when the fetus is abnormal;
   result report means for receiving a request to report the final report about the abnormal fetus from the main processor and providing data of informing that the fetus is abnormal to the data offering client through the communications network; and
   Web server managing means for transmitting the first analysis data to the data diagnosis clients through the communications network, receiving the final diagnosis result from the data diagnosis clients, stores the final diagnosis result in the database means and displaying the data stored in the database means on the homepage in order to provide all diagnosis processes from the source data to the final diagnosis result.

4. The telemetric system for fetal care as claimed in claim 3, wherein the data analysis program in the main processor includes:
   a fetal HR analysis module for evaluating Long-term/Short-term MMR (Mean Minute Range) with use of the fetal HR data extracted from the source data;
   a variability analysis module for analyzing a period of the UC data in order to set a time basis, calculating a fetal HR baseline with accumulating the fetal HR data extracted from the source data according to the time basis, and determining a pulse situation from the fetal HR baseline; and
   a fetal HR acceleration/deceleration analysis module for determining whether a fetal HR accelerates or decelerates with the fetal HR data.

5. The telemetric system for fetal care as claimed in claim 4, wherein the fetal HR acceleration/deceleration analysis module includes a module for detecting acceleration of the fetal HR and a module for detecting deceleration of the fetal HR.

6. The telemetric system for fetal care as claimed in claim 3, wherein the result report means display the final diagnosis result on the homepage through the Web server managing means for providing the final diagnosis result to a plurality of clients, and reports the final diagnosis result to the data offering client by any or all of e-mail, phone and ARS (Auto Response Service).

7. A telemetric method for fetal care comprising the steps of:
   a) receiving a source data from a pregnant woman and a fetal of the pregnant woman through a data offering client terminal which includes an data input unit and dividing the received source data into fetal heart rate (HR) data and uterine contraction (UC) data of the pregnant woman;
   b) making a provisional diagnosis for producing a first analysis data by analyzing the fetal HR data and the UC data;
   c) transmitting the first analysis data to Web server managing means to be displayed on a homepage and transmitting the first analysis data to result report means in case that the provisional diagnosis finds an abnormal result in order to report the abnormal result to the data offering client; and
   d) providing the first analysis data to a data diagnosis client according to a request of the data diagnosis client, receiving and storing a final diagnosis result from the data diagnosis client, transmitting the final diagnosis result to the Web server managing means, and reporting the final diagnosis result including normal/abnormal situation information to the data offering client.

8. The telemetric method for fetal care as claimed in claim 7,
   wherein the first analysis data includes variability data for determining fetal hypoxia,
   wherein the first analysis data further includes data about fetal HR acceleration, prolonged fetal HR acceleration, variable fetal HR deceleration, prolonged fetal HR deceleration, early fetal HR deceleration and late fetal HR deceleration for diagnosis of a fetal HR acceleration/deceleration by using the fetal HR data extracted from the source data.

9. The telemetric method for fetal care as claimed in claim 8, wherein the step b) further includes the steps of:
   1) calculating a Long-term MMR (Mean Minute Range) and a Short-term MMR from the fetal HR data;
   2) removing noise from the fetal HR data; and
   3) finding a stand deviation of the fetal HR data without noise.

10. The telemetric method for fetal care as claimed in claim 9,
    wherein the Long-term MMR of the step 1) is a value calculated by generating a first Long-term maximum variation value by converting a peak of the fetal HR data for a predetermined time into a msec unit, generating a second Long-term maximum variation value by converting a nadir of the fetal HR data for a predetermined time into a msec unit, accumulating and averaging differences between the first Long-term maximum variation value and the second Long-term maximum variation value.

11. The telemetric method for fetal care as claimed in claim 9,
wherein the Short-term MMR of the step 1) is a value calculated by generating a first Short-term maximum variation value by converting a peak of the fetal HR data for a predetermined time into a msec unit, generating a second Short-term maximum variation value by converting a nadir of the fetal HR data for a predetermined time into a msec unit, accumulating and averaging differences between the first Short-term maximum variation value and the second Short-term maximum variation value.

12. The telemetric method for fetal care as claimed in claim 9, wherein the step b) further includes the steps of:
4) determining that the fetal HR data is normal when being centered on a baseline of the fetal HR data, tachycardia when being faster than the normal HR data, and bradycardia when being slower than the normal HR data according to the predetermined baseline; and
5) determining variability data with the standard deviation of the baseline according to predetermined criteria.

13. The telemetric method for fetal care as claimed in claim 9, wherein the step b) further includes the step of:
6) determining whether the fetal HR data is normal or not, there is the fetal HR acceleration or not, and there is the prolonged fetal HR acceleration or not by detecting a wave of the fetal HR data, determining where the wave terminates and probing a peak in the nadir area of the wave.

14. The telemetric method for fetal care as claimed in claim 9, wherein the step b) further includes the steps of:
7) detecting a fetal HR deceleration wave by comparing the baseline of the fetal HR data with a basic fetal HR; and
8) detecting the variable fetal HR deceleration, the prolonged fetal HR deceleration, the early fetal HR deceleration and the late fetal HR deceleration in the fetal HR data with use of the fetal HR deceleration wave.

15. The telemetric method for fetal care as claimed in claim 7, wherein the step d) further includes the steps of:
storing the final diagnosis result transmitted from the data diagnosis client into database means; and
sending the final diagnosis result to the result report means and the Web server managing means in order to report the final diagnosis result to the data offering client with use of the result report means and display the final diagnosis result on the homepage through the Web server managing means.

16. The telemetric method for fetal care as claimed in claim 7,
wherein the data diagnosis clients include a first data diagnosis client for receiving and analyzing the first analysis data made in the step b) and generating second analysis data and a second data diagnosis client for collectively analyzing the source data and the second analysis data and producing the final diagnosis result.

17. A record medium including a telemetric diagnosis program for fetal care which transmits data from/to a client terminal and a Web server through a communications network, processing and analyzing the data and informing analyzed results, the record medium comprising:
a source data dividing process for receiving source data from a pregnant woman and a fetal of the pregnant woman through a data offering client terminal which includes an data input unit and dividing the received source data into fetal heart rate (HR) data and uterine contraction (UC) data of the pregnant woman;
a provisional diagnosis process for producing a first analysis data by analyzing the fetal HR data and the UC data;
a provisional diagnosis reporting process for transmitting the first analysis data to Web server managing means to be displayed on a homepage and transmitting the first analysis data to result report means in case that the provisional diagnosis finds an abnormal result in order to report the abnormal result to the data offering client; and
a final diagnosis result process for providing the first analysis data to a data diagnosis client according to a request of the data diagnosis client, receiving a final diagnosis result from the data diagnosis client, storing the final diagnosis result in a database, transmitting the final diagnosis result to the Web server managing means, and reporting the final diagnosis result including normal/abnormal situation information to the data offering client.

18. The record medium including a telemetric diagnosis program for fetal care as claimed in claim 17, wherein the provisional diagnosis process includes the steps of:
1) calculating a Long-term MMR (Mean Minute Range) and a Short-term MMR from the fetal HR data;
2) removing noise from the fetal HR data; and
3) finding a stand deviation of the fetal HR data without noise.

19. The record medium including a telemetric diagnosis program for fetal care as claimed in claim 18,
wherein the Long-term MMR of the step 1) is a value calculated by generating a first Long-term maximum variation value by converting a peak of the fetal HR data for a predetermined time into a msec unit, generating a second Long-term maximum variation value by converting a nadir of the fetal HR data for a predetermined time into a msec unit, accumulating and averaging differences between the first Long-term maximum variation value and the second Long-term maximum variation value.

20. The record medium including a telemetric diagnosis program for fetal care as claimed in claim 18,
wherein the Short-term MMR of the step 1) is a value calculated by generating a first Short-term maximum variation value by converting a peak of the fetal HR data for a predetermined time into a msec unit, generating a second Short-term maximum variation value by converting a nadir of the fetal HR data for a predetermined time into a msec unit, accumulating and averaging differences between the first Short-term maximum variation value and the second Short-term maximum variation value.

21. The record medium including a telemetric diagnosis program for fetal care as claimed in claim 18, wherein the provisional diagnosis step further comprises the steps of
4) determining that the fetal HR data is normal when being centered on a baseline of the fetal HR data, tachycardia when being faster than the normal HR data, and bradycardia when being slower than the normal HR data according to the predetermined baseline; and 5) determining variability data with the standard deviation of the baseline according to predetermined criteria.

22. The record medium including a telemetric diagnosis program for fetal care as claimed in claim 18, wherein the provisional diagnosis process further comprises the steps of:

6) determining whether the fetal HR data is normal or not, there is the fetal HR acceleration or not, and there is the prolonged fetal HR acceleration or not by detecting a wave of the fetal HR data, determining where the wave terminates and probing a peak in the nadir area of the wave.

23. The record medium including a telemetric diagnosis program for fetal care as claimed in claim 17, wherein the final diagnosis result process comprises the steps of:

storing the final diagnosis result transmitted from the data diagnosis client into database means; and sending the final diagnosis result to the result report means and the Web server managing means in order to report the final diagnosis result to the data offering client with use of the result report means and display the final diagnosis result on the homepage through the Web server managing means.

* * * * *